United States Patent [19]

Kanno et al.

[11] 4,409,088

[45] Oct. 11, 1983

[54] REGENERATION METHOD OF ION-SELECTIVE ELECTRODE, AND ION-SELECTIVE ELECTRODE AND ION-CONCENTRATION ANALYZER CONTAINING MEANS ADAPTED TO PRACTICE SAID METHOD

[75] Inventors: Ken-ichi Kanno, Tokyo; Tetsuya Gatayama; Masao Koyama, both of Yokohama, all of Japan

[73] Assignee: Tokyo Shibaura Denki Kabushiki Kaisha, Kawasaki, Japan

[21] Appl. No.: 391,133

[22] Filed: Jun. 23, 1982

[30] Foreign Application Priority Data

| Jun. 30, 1981 | [JP] | Japan | 56-100560 |
| Jun. 30, 1981 | [JP] | Japan | 56-100561 |
| Jun. 30, 1981 | [JP] | Japan | 56-100562 |
| Jun. 30, 1981 | [JP] | Japan | 56-100564 |
| Jun. 30, 1981 | [JP] | Japan | 56-100650 |

[51] Int. Cl.$^3$ ............................................. G01N 27/30
[52] U.S. Cl. .................................... 204/402; 134/25.4; 134/42; 204/409; 204/418
[58] Field of Search ............... 204/402, 418, 1 T, 409; 134/25.4, 42

[56] References Cited

U.S. PATENT DOCUMENTS

| 3,715,297 | 2/1973 | Cosgrove et al. | 204/418 |
| 4,190,481 | 2/1980 | Goffredo | 156/345 |
| 4,314,895 | 2/1982 | Spaziani et al. | 204/418 |

FOREIGN PATENT DOCUMENTS

| 54-26791 | 2/1979 | Japan | 204/418 |
| 1437091 | 5/1976 | United Kingdom | 204/418 |
| 1544939 | 4/1979 | United Kingdom | 204/17 |
| 1593270 | 7/1981 | United Kingdom | 204/418 |

OTHER PUBLICATIONS

*Patent Abstracts of Japan*, vol. 3, No. 48, p. 106, E106, Apr. 24, 1979.

H. Keller et al., "Ionen-selektive Elektroden zur Bestimmung von Urin-Elektrolyten," *Biomedizinische Technik*, vol. 25, No. 3, Berlin, Mar. 1980.

*Primary Examiner*—G. L. Kaplan
*Attorney, Agent, or Firm*—Schwartz, Jeffery, Schwaab, Mack, Blumenthal & Koch

[57] ABSTRACT

Disclosed is a method for regenerating an ion-selective electrode equipped with an ion-selective membrane which is formed of a polymer membrane containing an ion-selective material and plasticizer, which method comprises supplying to the ion-selective membrane a regenerating plasticizer which is either identical in every aspects or analogous in effects to the first-mentioned plasticizer and is capable of dissolving the ion-selective material therein and imparting flexibility to the ion-selective membrane. Also disclosed are several embodiments of ion-selective electrodes and ion-concentration analyzers containing means for practicing said method.

14 Claims, 15 Drawing Figures

REGENERATION METHOD OF ION-SELECTIVE ELECTRODE, AND ION-SELECTIVE ELECTRODE AND ION-CONCENTRATION ANALYZER CONTAINING MEANS ADAPTED TO PRACTICE SAID METHOD

This invention relates to a method for regenerating an ion-selective electrode whose ion-selective membrane has been degraded in activity, and an ion-selective electrode and an ion-concentration analyzer containing means adapted to practice said method.

An ion-selective electrode is an analytical device for selectively and quantitatively determining a specific ionic species present in a solution. Such ion-selective electrodes have heretofore been employed in an extensive technical field, for example, to monitor the concentrations of specific ionic species and to analyze the quality of water.

Ion-selective electrodes generally have such a structure as schematically illustrated in FIG. 1. Basically, an ion-selective electrode is formed of a cylindrical electrode casing 12 defining an opening 11 at one end thereof, made of a material insoluble in a test solution (e.g., polyvinyl chloride) and having a hollow cylindrical shape (e.g., circular cylinder); an ion-selective membrane 13 attached, for example adherently, to the opening 11 and hermetically closing the opening 11; a partition wall 16 forming a first cell 14 containing the opening 11 and a second cell 15 positioned opposite to the opening 11; an ion-conductive material 14' such as an electrolytic solution filled in the first cell 14; an internal reference electrode 17 kept in place by the partition wall 16 and immersed in the ion-conductive material 14' sealed perfectly by the said wall 16; and lead 18 extending from the internal reference electrode 17 to the outside of the cylindrical electrode casing 12 through the second cell 15.

The determination of the concentration of a specific ion species is carried out by immersing a free end portion of the electrode, in other words, a part of the electrode which part contains the ion-selective membrane 13 in a test solution.

The ion-selective membrane 13 is a flexible, polymer membrane which, when the electrode is immersed in a test solution, acts selectively to a specific ion species, i.e., a particular target ion species present in the test solution. Where such target ion species are $NH_4^+$, $Na^+$ and $K^+$, an ion-selective material such as nonactin; monensin, nigericin or crown ethers; or valinomycin or crown ethers and a plasticizer such as dioctyl adipate, dioctyl phthalate, dibutyl sebacate, dibutyl phthalate, tricresyl phosphate, diamyl phthalate or dodecyl phthalate are incorporated in predetermined proportions in a polymer such as polyvinyl chloride or polycarbonate. The thus-compounded polymer is then formed into a sheet by a method commonly known in the art, thereby obtaining an ion-selective membrane.

When such an ion-selective electrode is immersed in a test solution, the electrode indicates a potential E which is connected with the activity a of a specific ionic species present in the test solution, as shown by the Nernst equation represented by the following style:

$$E = E^\circ \pm 2.303(RT/ZF) \log a$$

wherein R, T, Z, F and E° mean respectively the gas constant, the temperature of the test solution expressed in terms of absolute temperature, the ionic valence of the specific ion species, the Faradic constant and the standard potential of the system, the (+) sign is employed when a is cationic activity, and the (−) sign is followed when a is anionic activity. As a result, the activity of the specific ion species can be readily calculated from a potential value of the system determined.

Therefore, use of an ion-selective electrode permits the determination of concentration of specific ion species over a wide concentration range by simply measuring potentials of the electrode. Furthermore, a test solution of a small volume may still be subjected to an ion-concentration measurement provided that the ion-selective electrode is formed in a small size.

Since ion-selective electrodes are very convenient as mentioned above, they have recently found a wide spread utility for clinical purposes, particularly, for the quantitative analyses of various ions dissolved in blood, for example, $K^+$, $Na^+$ and $Cl^-$.

However, the activity of an ion-selective membrane is gradually degraded while the ion-selective electrode is used over a long period of time, since certain components of the ion-selective membrane may be eluted into the test solution or certain impurities in the test solution may, in contrast with this, be caught in the ion-selective membrane. As a result of a further research carried out by the present inventors, it was surprisingly found that, among various components of each ion-selective membrane, it is a loss of the plasticizer through its elution that principally causes its degradation. The mechanism of the degradation of an ion-selective membrane may be explained as follows. Namely, when the plasticizer contained in the ion-selective membrane is lost through its elution, an ion-selective material also present in the ion-selective membrane deposits in the membrane and its complex-forming ability with an intended specific ion species is decreased or its mobility within the membrane is lowered, thereby failing to show the Nernstian response. Especially, the life time of an ion-selective electrode becomes considerably shorter when blood or serum is used as a test solution, because blood or serum has a nature similar to surfactants and some specific component(s) is extracted into the blood or serum from the membrane or the ion-selective membrane is susceptible to erosion by bacteria or the like present in blood or serum, and, as a result, no Nernstian response would be available at the ion-selective electrode even after using it for a short period of time. This is certainly serious problem to users.

To cope with the above problem, there have been taken some countermeasures, including to discard a degraded ion-selective electrode and substitute therefor a new ion-selective electrode or to remove the degraded ion-selective membrane from a degraded ion-selective electrode and put a new ion-selective membrane on the ion-selective electrode whenever the degradation of the ion-selective membrane has proceeded and the Nernstian responses become unavailable. However, these prior art countermeasures were not preferred since the former countermeasure leads to the wasting of costly ion-selective electrodes and is thus disadvantageous from the economical viewpoint while, in the latter countermeasure, the replacement work of ion-selective membranes are extremely difficult and time-consuming.

It has been proposed, as a solution to such problems, to immerse for a certain time period an ion-selective electrode whose membrane activity has been degraded in a solution containing practically the same components as all the components of the ion-selective membrane dissolved in a solvent such as, for example, tetrahydrofuran and then to drive off the solvent for the activation and regeneration of the ion-selective electrode (see, Japanese Patent Laid-open Application No. 26791/1979).

According to the above proposal, a membrane-regenerating solution obtained by dissolving the components of the membrane in an organic solvent is applied to the membrane and the organic solvent is thereafter caused to evaporate to obtain the regenerated ion-selective electrode in a dry state. Thus, all the components of the regenerating solution may not be supplied satisfactorily into the degraded membrane bulk and, in some instances, a fresh ion-selective membrane may be formed over the degraded membrane. Accordingly, the above-proposed regeneration method did not always bring about satisfactory results. It is also accompanied by another inconvenience that, when an ion-selective electrode is immersed for a sufficiently long time period in the above regenerating solution with a view to obtaining satisfactory regeneration effects, its ion-selective membrane will be dissolved in its entirety due to the action of the solvent. It also involves, as one of its drawbacks, an economical disadvantage because the regenerating solution contains a variety of the same components as the ion-selective membrane and is hence expensive.

The present inventors have carried out a series of extensive researches with a view toward solving the drawbacks of the last-mentioned prior art regeneration method. As a result, it has been revealed unexpectedly that the activity of an ion-selective membrane can be regenerated to show the Nernstian responses again by, taking into consideration that the loss of its plasticizer through elution is a principal cause for the degradation of the membrane, bringing the ion-selective membrane into contact with a plasticizer which is either identical in every aspects or analogous in effects to the plasticizer contained in the degraded ion-selective membrane and is capable of dissolving therein an ion-selective material which is another component of the membrane, and also imparting flexibility to the membrane. On the basis of the above finding, the present invention has been completed.

An object of this invention is thus to provide a method for regenerating an ion-selective electrode whose membrane activity has been degraded and means to practice the method. In one aspect of this invention, there is accordingly provided a method for regenerating an ion-selective electrode equipped with an ion-selective membrane which is formed of a polymer membrane containing an ion-selective material and plasticizer, which method comprises supplying to the ion-selective membrane a regenerating plasticizer which is either identical in every aspect or analogous in effects to the first-mentioned plasticizer and is capable of dissolving the ion-selective material therein and imparting flexibility to the ion-selective membrane.

As exemplary polymer materials suitable for use in the production of the ion-selective membrane according to this invention, may be mentioned polyvinyl chloride, polyurethane, silicone rubber, polystyrene, polymethyl methacrylate, etc. On the other hand, ion-selective materials suitable for use in this invention include for example, valinomycin, dibenzo-19-crown-6, dicyclohexyl-18-crown-6, nonactin, dinactin, trinactin, tetranactin, gramicidin, monensin, nigericin, methyltridecylammonium chloride, methyltricaprylammonium chloride, etc. Exemplary plasticizers usable in this invention may include dioctyl adipate, diisodecyl adipate, dioctyl phthalate, diisodecyl phthalate, dioctyl sebacate, tricresyl phosphate, ortho-nitrophenyl octyl ether, and the like.

In the present invention, it is desirous to use, as a regenerating plasticizer, the same plasticizer as that contained in an ion-selective membrane to be regenerated. Plasticizers other than that contained in the membrane may also be employed as regenerating plasticizers so long as they can dissolve an ion-selective material present in the membrane and can also impart flexibility to the membrane. More specifically, the above-recited plasticizers may be employed solely or in a suitable combination.

There will hereinafter be described, with reference to the accompanying drawings, certain embodiments of the method of regenerating an ion-selective electrode, which is performed by supplying such plasticizer to its degraded. ion-selective membrane.

In the drawings:

FIGS. 1, 5 and 6 illustrate schematically ion-selective electrodes;

FIGS. 2, 3, 4, 7 and 8 show individually the response potential of a potassium ion-selective electrode as a function of the concentration of potassium ions and time; Completely degraded (i.e., failed) potassium ion-selective electrodes were employed in FIGS. 2 and 7 while potassium ion-selective electrodes regenerated in accordance with the first embodiment of the method according to this invention were used in FIGS. 3, 4 and 8; In each of the diagrams, the wave forms 1, 2 and 3 represent respectively response potentials at $K^+ = 10^{-5}$ M, $K^+ = 10^{-3}$ M, and $K^+ = 10^{-1}$ M;

FIG. 11 is a schematic illustration of the electrode whereas FIG. 12 is an enlarged fragmentary cross-sectional view of a free end portion of the electrode;

Figure 13:
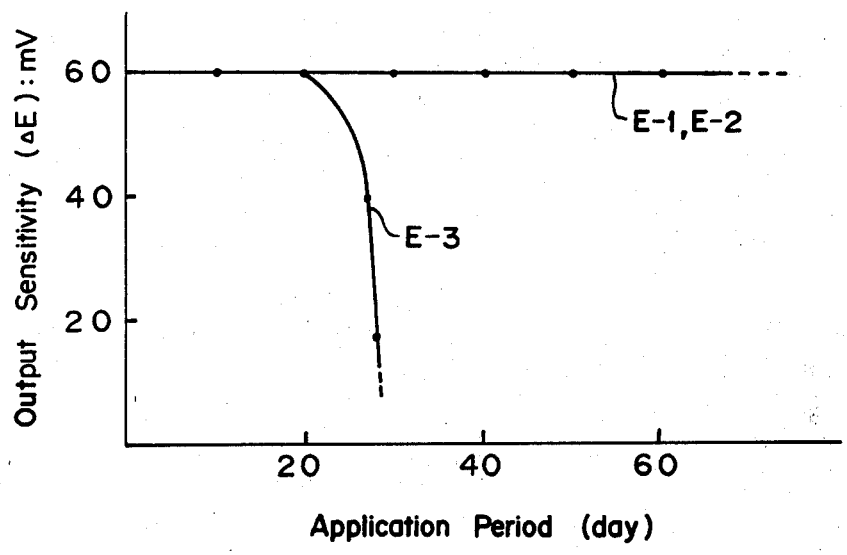
Figure 14:
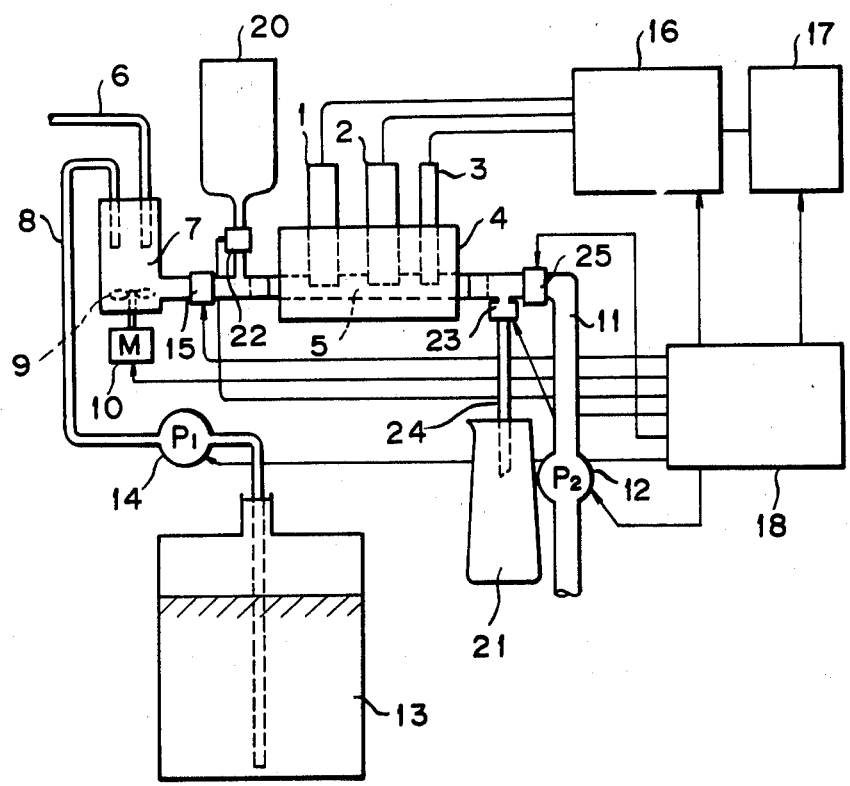
Figure 15:
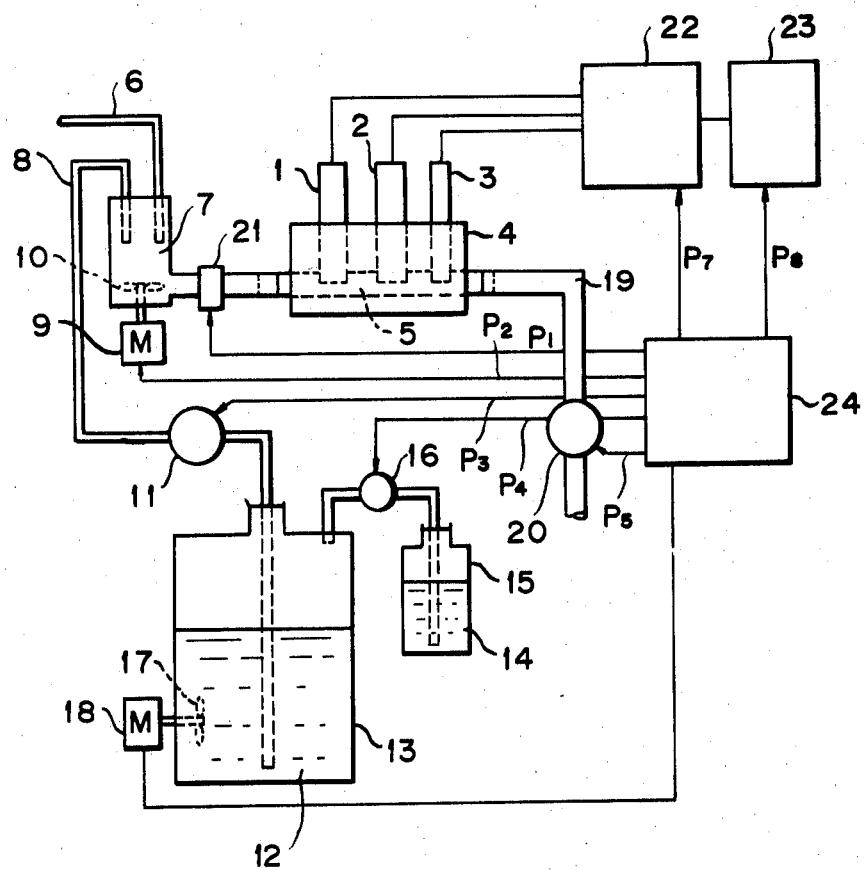

FIG. 13 diagrammatically illustrates the output potentials of ion-selective electrodes as a function of time, and shows the performance of ion-selective electrodes according to this invention in comparison with that of an ion-selective electrode of a conventional structure;

FIG. 14 is a simplified functional block diagram of an ion-concentration analyzer employed in the fourth embodiment of this invention; and FIG. 15 is a simplified functional block diagram of an ion-concentration analyzer employed in the fifth embodiment of this invention.

The first embodiment of this invention may be carried out by either one of various simple methods, for example, by immersing a part of a degraded ion-selective electrode which part contains its membrane in a plasticizer for a certain period of time while maintaining the membrane on the electrode; by wiping the outer surface of the electrode with absorbent cotton soaked with the plasticizer; or by holding the electrode upright with the outer surface of its membrane up and dropping the plasticizer onto the membrane. Among such regeneration methods, it is most desirous to immerse the outer surface of the membrane of an electrode in a plasticizer in view of its simplicity and reliableness.

The first embodiment of this invention will hereinafter be described in further detail with reference to the following example.

Figure 1:
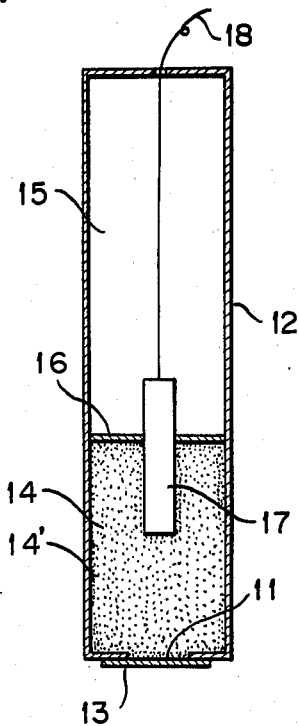

Nine potassium ion-selective electrodes were provided, each having a structure as shown in FIG. 1 and being constructed of a cylindrical electrode casing made of polyvinyl chloride, a potassium chloride solution (concentration: 0.1 M) as its ion-conductive material, a silver/silver chloride electrode as its internal reference electrode, and an ion-selective membrane of a polyvinyl chloride membrane containing valinomycin as its ion-selective material and dioctyl adipate as its plasticizer.

These nine electrodes were immersed in human serum at room temperature for one month. Then, the electrodes were pulled out of the human serum. Three electrodes out of these electrodes were thereafter dipped respectively in three potassium chloride solutions whose $K^+$ concentrations were respectively $10^{-5}$ M, $10^{-3}$ M and $10^{-1}$ M. Here, the potential of each electrode was measured along the passage of time. Results are shown in FIG. 2, in which wave form 1, wave form 2 and wave form 3 correspond respectively to $K^+$ concentrations of $10^{-5}$ M, $10^{-3}$ M, and $10^{-1}$ M.

Figure 2:
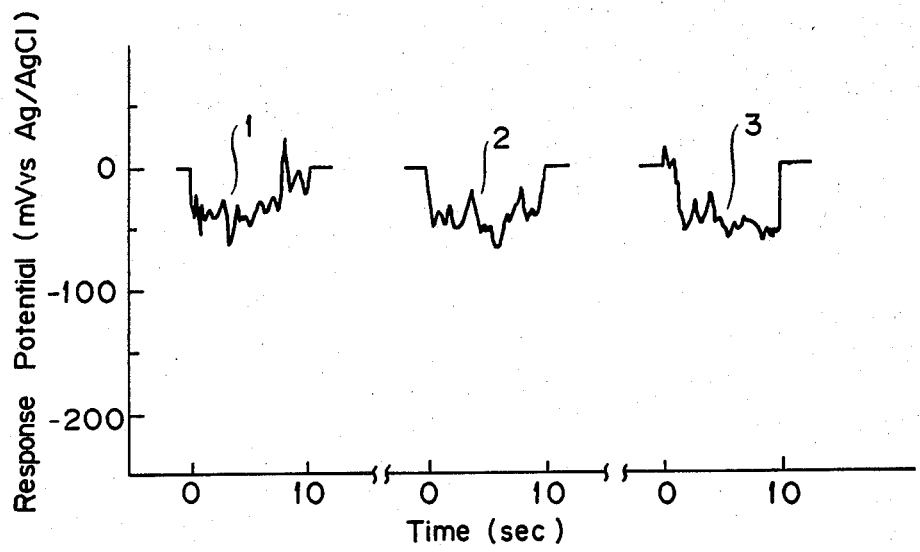

As readily envisaged from FIG. 2, it was observed that all the potassium ion-selective membranes were completely degraded because the electrodes failed to show the Nernstian response to variations in $K^+$ concentration and the response potentials contained considerably large noises.

Then, next three electrodes were dipped for about one hour in dioctyl adipate and the time dependence of the potential of each of the electrodes was determined in the same manner as that followed with respect to the first three electrodes. Results are shown in FIG. 3, in which the wave forms have the same significance as in FIG. 2.

Figure 3:
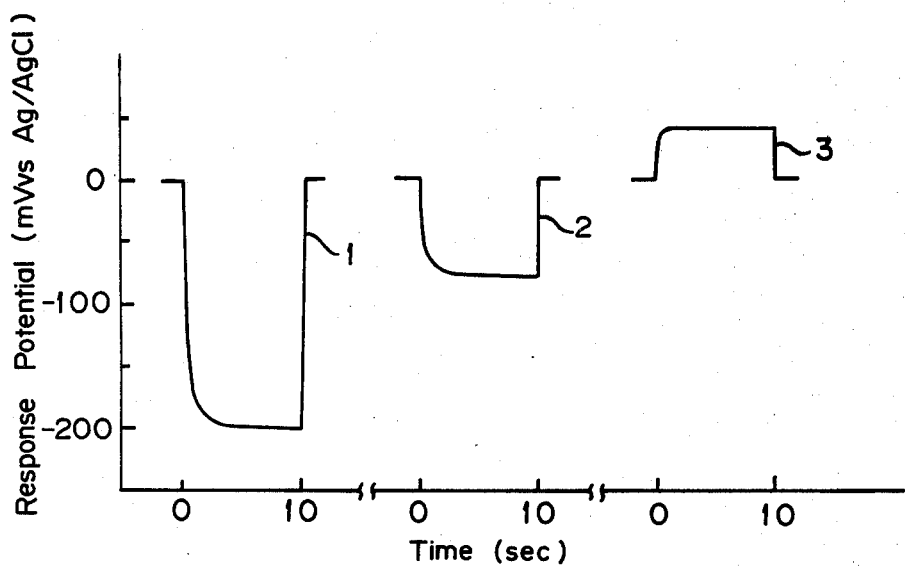

As apparent from FIG. 3, the electrodes treated in accordance with the first embodiment of the regeneration method of this invention showed a Nernstian responce of 59.0 mV potential change for a $K^+$ concentration change of 10 times and their response potentials were completely free of noise. It was also found that their response speeds were fast and their 99% responses had been completed in 5 seconds after their immersion in their respective potassium chloride solutions.

Figure 4:
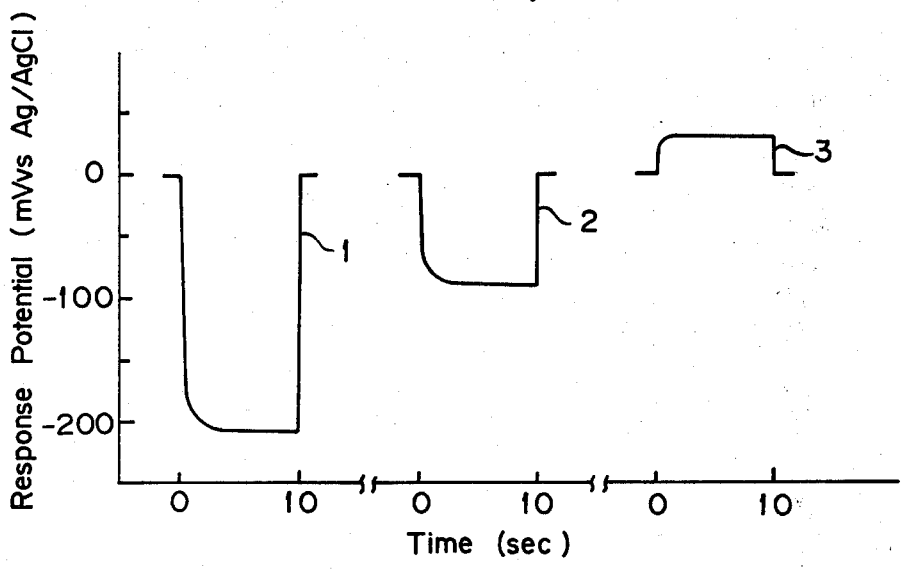

Finally, the remaining three electrodes were dipped for about 3 hours in dioctyl phthalate and potentials were caused to occur in the same manner as that employed above. The time dependency of the potentials were observed, also, following the manner employed above. Results are shown in FIG. 4, in which each wave form has the same significance as in FIGS. 2 and 3. FIG. 4 teaches clearly that dioctyl phthalate brought about exactly the same results as dioctyl adipate, both being used as regenerating plasticizers.

Figure 5:
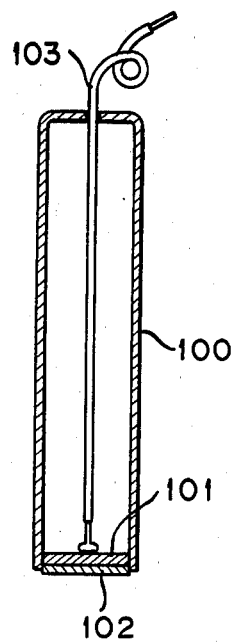
Figure 6:
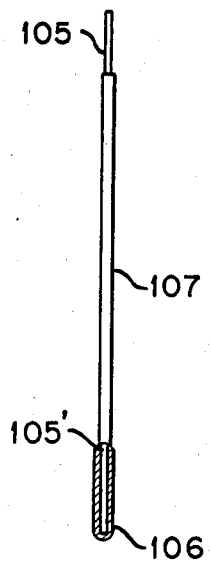

Besides the above-described ion-selective electrodes of the neutral carrier type which confine an inner electrolytic solution, the regeneration method according to the first embodiment of this invention may be equally applied to such ion-selective electrodes as shown in FIGS. 5 and 6, which electrodes do not contain any inner electrolytic solution but have a polymer membrane containing a neutral carrier in direct contact with a metal surface.

FIG. 5 depicts a potassium ion-selective electrode of such a type that an ion-selective membrane 102 of the neutral carrier type is kept in direct contact with a surface of a disc-shaped copper plate 101 attached to the free end of an electrode casing 100 made of polyvinyl chloride. The above ion-selective membrane 102 is made of polyvinyl chloride compounded with dioctyl adipate as a plasticizer and valinomycin as a potassium ion-selective neutral carrier. Incidentally, numeral 103 designates a lead which is soldered at one end thereof with the copper plate 101. A potential corresponding to each potassium ion concentration can be measured through the lead.

FIG. 6 shows a potassium ion-selective electrode of the exposure type, i.e., having no electrode casing such as for example the electrode casing 100 in FIG. 5. A polyvinyl chloride membrane 106 of the neutral carrier type is directly in contact with a tip portion 105' of a copper wire 105. The composition of the ion-selective membrane 106 is the same as that illustrated in FIG. 5. Designated at numeral 107 is an insulative shieth which electrically insulates the copper wire 105 except for its both tip portions.

Figure 7:
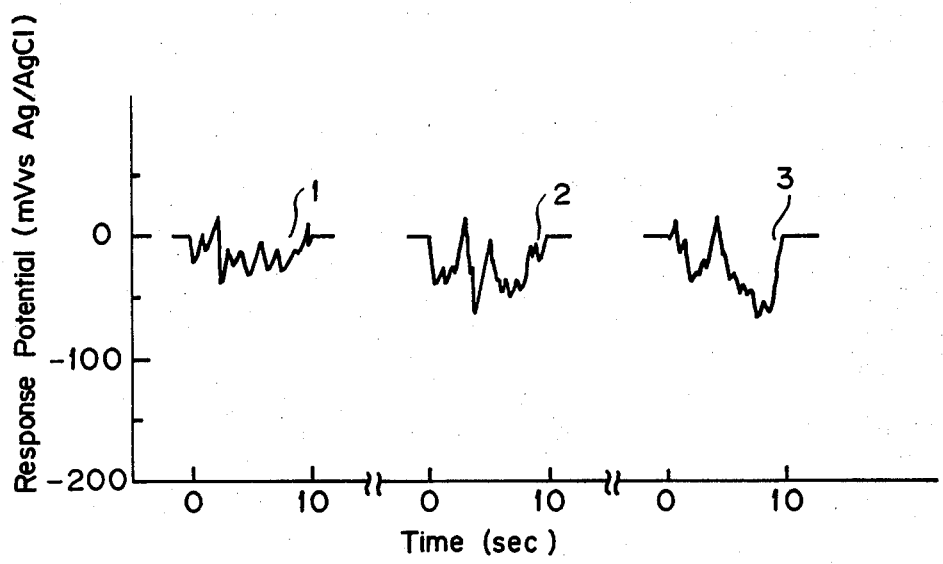

The electrodes shown in FIGS. 5 and 6 were immersed in human serum at room temperature for 35 days. Thereafter, the electrodes were taken out of the serum and successively dipped in three potassium chloride solutions of $10^{-5}$ M, $10^{-3}$ M and $10^{-1}$ M respectively. It was confirmed that the potassium ion-selective membranes had been completely degraded since the electrodes failed to show any Nernstian response and their response potentials contained extremely large noises. A response curve (i.e., the time dependency of potential) of an ion-selective electrode of the same type as shown in FIG. 5 is shown, merely by way of example, in FIG. 7.

Figure 8:
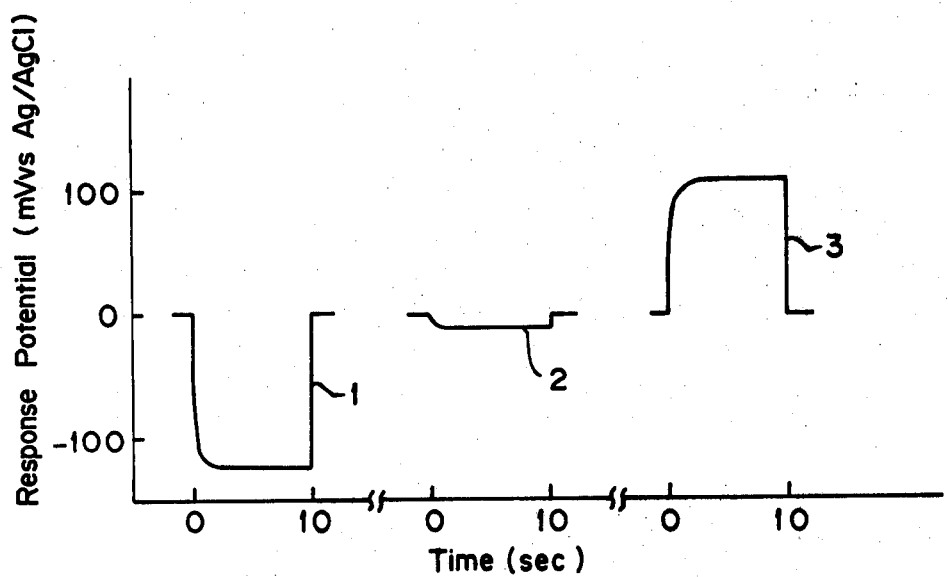

Then, the above two electrodes were dipped for about one hour in dioctyl adiapte and their potentials were measured along the passage of time in the same manner as mentioned above. Test results obtained on the electrode given in FIG. 5 are shown, merely by way of example, in FIG. 8. As seen readily from FIG. 8, the electrode treated in accordance with the regeneration method according to the first embodiment of this invention showed a Nernstian response of 59.0 mV potential change for a $K^+$ concentration variation of 10 times. Moreover, its response potential did not contain any noise. It was also found that its response speed was accelerated and the 99% response was completed in 5 seconds after immersing the electrode in the potassium chloride solution. As mentioned above, FIG. 8 corresponds to the electrode of the type shown in FIG. 5. An electrode of the type as shown in FIG. 6 was also regenerated in much the same way and showed Nernstian responses.

Both of the above electrodes, which had been subjected to regeneration, showed normal responses again and their life time were practically comparative with their initial life time. Accordingly, it has been confirmed that an electrode can be used for a time period substantially twice as long as its initial life time when it is regenerated once.

As has been described above, the regeneration method according to the first embodiment of this invention is capable of regenerating with extreme ease an ion-selective electrode, whose ion-selective membrane has been degraded, by using an inexpensive plasticizer. Thus, the regeneration method has a great industrial value.

By the way, the ion-selective electrodes were regenerated from their completely degraded states in the above example. Needless to say, the regeneration method according to the first embodiment of this invention may also be applied to ion-selective electrodes whose ion-selective membranes have not yet been degraded completely and are thus still capable of showing Nernstian responses but whose response speeds have become somewhat slower.

An ion-selective electrode, which is in actual use for the determination of concentration of a specific ion species may be readily prolonged in life time by dipping it periodically in such a plasticizer for a short time period.

As the second embodiment of this invention, the regenerating plasticizer may be supplied to a degraded ion-selective membrane by employing an ion-selective electrode in which the ion-selective membrane comprises an ion-selective material and plasticizer as well as a carrier containing the regenerating plasticizer either identical in every aspects or analogous in effects of the initial plasticizer.

According to one aspect of the second embodiment of this invention, there is thus provided an ion-selective electrode equipped with a casing filled with an electrically conductive material, an ion-selective membrane attached to a free end portion of the casing, an inner reference electrode supported within the casing and a lead connected to the internal reference electrode. The ion-selective membrane contains a high polymer as its base material, the high polymer contains in turn an ion-selective material and plasticizer as well as a carrier containing therein another plasticizer, and the latter plasticizer is present in concentration higher than the former plasticizer.

In the ion-selective electrode according to the second embodiment of this invention, its ion-selective membrane is formed of a high polymer membrane which contains an ion-selective material and plasticizer as well as a carrier containing therein another plasticizer. The carrier is dispersed throughout the ion-selective membrane and contains the latter plasticizer in a relatively high concentration so that, when the former plasticizer in the ion-selective material has diffused in a test solution, the latter plasticizer is allowed to supplementarily penetrate into the ion-selective membrane from the carrier. Thus, care must be taken to make the ion-selective electrode in such a manner that the concentration of the plasticizer contained in the carrier, which is in turn contained in the ion-selective membrane, is sufficiently higher than that of the plasticizer contained in the same ion-selective membrane.

Namely, the ion-selective membrane of an electrode according to the second embodiment of this invention may be prepared for example, by adding and mixing in a solution of a high polymer, which solution contains 5 wt.% of an ion-selective material and 60 wt.% of a plasticizer, a finely pulverized carrier which contains another plasticizer identical in every aspects to the former plasticizer in such a concentration that the latter plasticizer contained in the carrier is much higher than the former plasticizer.

As the carrier in the second embodiment of this invention, may be mentioned diatomaceous earth, activated carbon, silica gel, alumina, activated clay, molecular sieve or the like.

The amount of the ion-selective material contained in the ion-selective membrane used in the second embodiment of this invention may vary depending on the type of the ion-selective material. Generally speaking, it may be contained in an amount of 0.5~30 wt.%. On the other hand, the carrier may be contained in an amount of, generally, 1~5 wt.% and preferably, 2~3 wt.%. The carrier may be saturated with the regenerating plasticizer.

Figure 9:
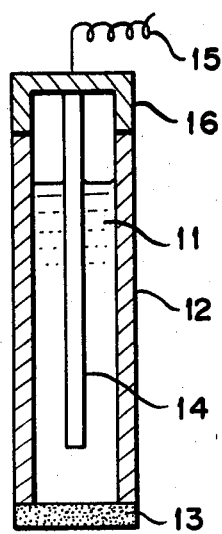
FIG. 9 is a cross-sectional view of an ion-selective electrode employed in the second embodiment of the present invention.

The ion-selective electrode according to the second embodiment of this invention is constructed, as shown in FIG. 9, by a tubular casing 12 containing in the interior thereof an electrically conductive material 11 which serves as an electrolytic solution, a potassium ion-selective membrane 13 adherently attached to a free end portion of the casing 12, an internal reference electrode 14 supported within the casing 12, a lead 15 connected to the internal reference electrode 14 and a cap 16 provided on the top of the casing 12 and allowing the lead 15 to extend therethrough. The ion-selective membrane 13 is prepared, as a potassium ion-selective membrane of 180 $\mu$m in thickness, by thoroughly mixing and dissolving 0.5 g of polyvinyl chloride as a polymer, 20 mg of valinomycin as an ion-selective material, 1 g of dioctyl adipate as a plasticizer and 1 mg of potassium tetraphenylborate in 20 ml of tetrahydrofuran, adding a plasticizer-containing carrier, which has been obtained on the side by impregnating 50 mg of diatomaceous earth (Cerite 545) of 80~100 mesh thoroughly with 50 mg of dioctyl adipate, to the above solution of the high polymer and promptly dispersing the carrier therein, and then pouring the thus-obtained dispersion in its entirety into a shallow dish having an inner diameter of 9 cm and drying the same.

Figure 10:
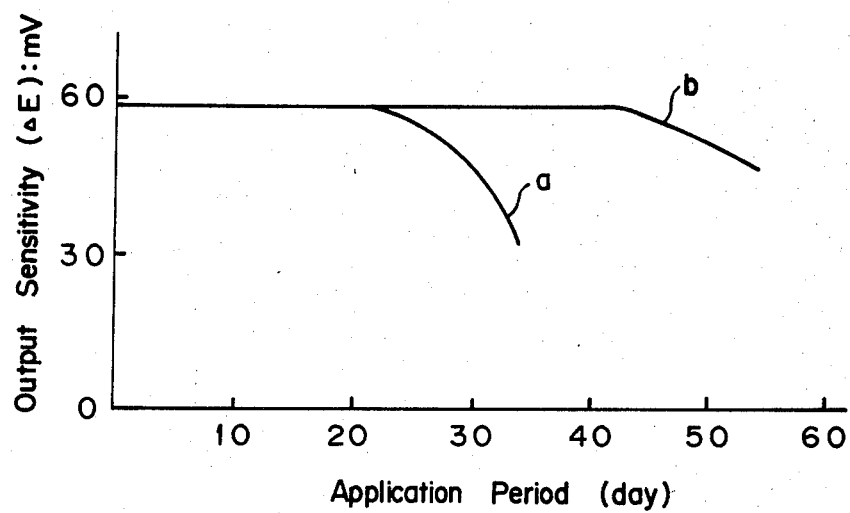
FIG. 10 is a diagram showing a characteristic curve of the electrode depicted in FIG. 9 in comparison with that of a conventional ion-selective electrode.

In order to determine the performance of the thus-obtained ion-selective electrode, it was compared in performance with a conventional ion-selective membrane which had been prepared with the same composition except for the exclusion of the plasticizer-containing carrier. In FIG. 10, the curve a represents an ion-selective electrode equipped with the conventional potassium ion-selective membrane while the performance of the ion-selective electrode according to the second embodiment of this invention is represented by the curve b. FIG. 10 shows the output sensitivity ($\Delta E$), which represents a change in potential produced in response to a potassium activity change of 10 times, as a function of the number of application days. It is readily envisaged that the electrode according to the second embodiment of this invention is assured to enjoy a longer usable period than the conventional electrode.

As apparent from the above comparison, the ion-selective electrode according to the second embodiment of this invention is capable of maintaining the concentration of the plasticizer in its membrane without losing it through its diffusion into test liquids and avoiding the reduction in complex-forming capacity of its ion-selective material, owing to the presence of the carrier dispersed in the ion-selective membrane which carrier has been finely pulverized and soaked sufficiently with a plasticizer.

The second embodiment of this invention may also be applied to such electrodes as shown in FIGS. 5 and 6.

As the third embodiment of this invention, the plasticizer may be supplied to a degraded ion-selective membrane for its regeneration by using an electrode which contains a built-in plasticizer-supplying pocket filled with a plasticizer either identical in every aspects or analogous in effects to the plasticizer contained in the ion-selective membrane in such a way that a part of the boundary wall of the pocket is formed of a part of the ion-selective membrane.

In one aspect of the third embodiment of this invention, there is thus provided an ion-selective electrode including a hollow cylindrical electrode casing defining an opening at one end thereof, an ion-selective membrane hermetically attached over the opening and made of a polymer membrane containing an ion-selective material and plasticizer, a partition wall dividing the interior of the cylindrical electrode casing into a first cell including the opening and a second cell positioned opposite to the opening, an ion-conductive material sealed in the first cell, an inner reference electrode immersed in the ion-conductive material and kept in place by the partition wall and a lead extending from the inner reference electrode to the outside of the cylindrical electrode casing through the second cell. The electrode further comprises a third cell which is a pocket formed in a base portion of the first chamber and includes a part of the ion-selective membrane as a part of its boundary wall, said third cell being filled with a plasticizer which is either identical in every aspects or analogous in effects to the plasticizer contained in the ion-selective membrane and is capable of dissolving the ion-selective material therein and imparting flexibility to the ion-selective membrane; an air flow passage extending from the third cell to the second cell; and another membrane hermetically attached over the opening of the air flow passage into the second cell, said membrane being permeable to air but impervious to the plasticizer in the third cell.

An ion-selective electrode according to the third embodiment of this invention will hereinafter be described with reference to FIGS. 11 and 12.

Figure 11:
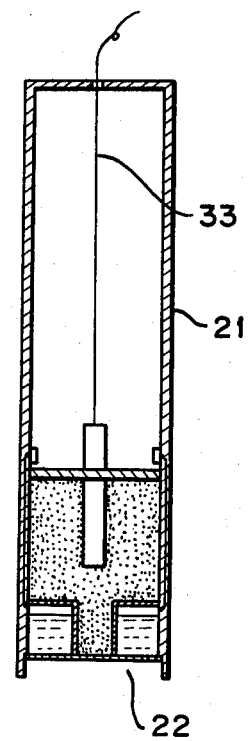
FIGS. 11 and 12 show an example of the ion-selective electrode used in the third embodiment of this invention.
Figure 12:
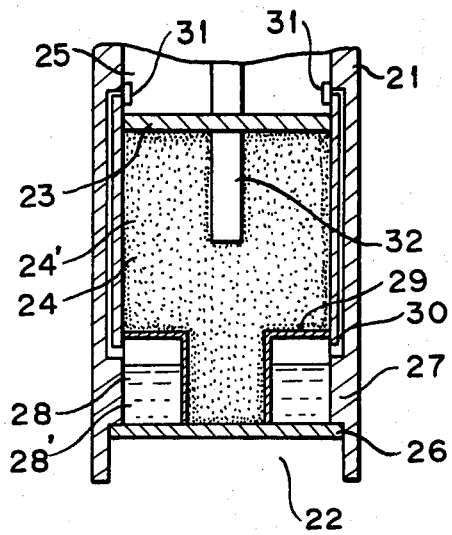

In FIGS. 11 and 12, numeral 21 indicates an internally hollow, cylindrical electrode casing prolonged in its entirety (for example, a circular cylindrical casing). It is open at one end (at the bottom in the drawings) to define an opening 22 but closed at the other end (i.e., at the top in the drawing). Designated at numeral 23 is a partition wall which divides the interior of the cylindrical electrode casing 21 into a first cell 24 containing the opening 22 and a second cell 25 assuming an upper position in the drawings.

An ion-selective membrane is indicated at numeral 26 and hermetically closes the opening 22 of the cylindrical electrode casing 21. The hermetic closure of the opening 22 is carried out by adhering a peripheral edge portion of the ion-selective membrane 26 to a casing wall 27 of the cylindrical electrode casing 21 with a suitable adhesive.

The first cell 24 is filled with an ion-conductive material 24' which contains the specific ion species, identical to ions to be measured, and, needless to say, must be at its surface in direct contact with the ion-selective membrane 26.

Numeral 28 represents the third cell which features structurally the electrode according to the third embodiment of this invention. The third cell 28 is formed in a base portion of the first cell 24 and includes as parts of tis boundary wall a part of the ion-selective membrane 26 and a part of the casing wall 27. Another part of the boundary wall is formed of a wall 29. The third cell 28 can form an isolated internal pocket within the first cell 24 by, for example, adhering the lower edge of the upright wall portion of the wall 29 to the ion-selective membrane 26 as shown in the drawings. A plasticizer 28' of the same type as mentioned above is then filled in the thus-formed pocket and is kept at its surface in direct contact with the ion-selective membrane 26.

Upon forming the third cell 28, it is essential to form a part of its boundary wall by a part of the ion-selective membrane 28. Otherwise, the plasticizer 28' filled in the third cell 28 is unable to contact with the ion-selective membrane 26, resulting in a failure to achieve the effect of the third embodiment of this invention.

The above-mentioned third cell 28 may be formed in an annular shape along the entire peripheral portion of the base portion of the first cell 24. Alternatively, it may be formed as a plurality of mutually-isolated pockets. It is however indispensable that a part of its boundary wall (for example, its bottom wall) be formed of the ion-selective membrane irrespective of its shape or location.

At numeral 30, there is shown an air flow passage which is bored through the casing wall 27 from a point above the level of the plasticizer 28' but still within the third cell 28 to the second cell 25. The air flow passage 30 serves to avoid the development of a negative pressure and its progress in the third cell 28, which negative pressure would otherwise arise as the plasticizer 28' in the third cell 28 diffuses into the ion-selective membrane 26. Thus, the upper opening of the air flow passage 30 which opening opens into the second cell 25 is sealed with another membrane 31 which is permeable to air but impervious to the plasticizer 28'. As such a membrane, may be mentioned for example a cellulose acetate membrane or TEFLON membrane. In the illustrated embodiment, the air flow passage 30 is bored through the interior of the casing wall 27. However, the air flow passage 30 shall not be limited to such an embodiment. For example, it may still be possible to form such an air flow passage by a thin, hollow pipe which extends through the wall 29, second cell 24 and partition wall 23.

Numeral 32 indicates an internal reference electrode immersed in the ion-conductive material 24'. The internal reference electrode 32 is hermetically held in place by the partition wall 23 and protrudes at an uppon part thereof into the second cell 25. A lead 33 is connected to the upper extremity of the internal reference electrode 32 so as to deliver electric signals (potentials) of the internal reference electrode 32. The lead 33 extends through the second cell 25 to the outside of the system.

Owing to the above-mentioned construction, the ion-selective membrane is always supplied with the plasticizer and it is thus possible to prevent the degradation of the membrane activity which would otherwise occur due to a loss of the plasticizer from the ion-selective membrane through its elution when immersed in a test liquid for a long period of time.

For the sake of comparison, an electrode (E-1) of a structure as shown in FIGS. 11 and 12 was fabricated by using a potassium ion-selective membrane made of polyvinyl chloride compounded with valinomycin and dioctyl adipate as the ion-selective membrane 26, a potassium chloride solution as the ion-conductive material 24, a silver/silver chloride electrode as the internal reference electrode 32 and a thin TEFLON membrane as the membrane 31 and by filling dioctyl adipate in the third cell 28. Another electode (E-2) of the same structure as the electrode E-1 was also produced following the above procedure except that dioctyl phthalate was filled in the third cell in place of dioctyl adipate. Needless to say, the above electrodes E-1 and E-2 are embraced by the third embodiment of this invention. A further electrode (E-3) of a structure as shown in FIG.

1 was also produced using the same parts as employed to make the electrodes E-1 and E-2.

These three electrodes were dipped in serum having a $K^+$ concentration of $4.4 \times 10^{-3}$ M and maintained at 37° C. With respect to each of the electrodes, the potential difference $\Delta E$ between the above serum and its 10 times dilution ($K^+$ concentration: $4.4 \times 10^{-4}$ M) was observed along the passage of time. Each electrode was immersed in the serum for 8 hours a day.

Results of the above test are shown in FIG. 9. As apparent from the drawing, it was found that the ion-selective electrodes according to the third embodiment of this invention (E-1 and E-2) has considerably longer life time compared with the conventional ion-selective electrode (E-3).

In each of the above examples pertaining the third embodiment of this invention, the ion-conductive material and plasticizer are housed independently in separate cells. However, the third cell may be obviated provided that a plasticizer capable of dissolving a hydrophobic ion-conductive material but incapable of dissolving the cylindrical electrode casing is filled together with the hydrophobic ion-conductive material in the first cell (for instance, a system consisting of methyltrioctylammonium chloride as a hydrophobic ion-conductive material and dioctyl adipate as a plasticizer; or another system consisting of potassium tetraphenylborate as a hydrophobic ion-conductive material, dioctyl adipate as a plasticizer and nitrobenzene as a solvent). Here, it is also possible to avoid the dissolution of the ion-selective material from the ion-selective membrane into the plasticizer when the ion-selective material is before-hand dissolved in the plasticizer.

As has been described above, the ion-selective electrode according to the third embodiment of this invention has considerably prolonged life time and is thus assured to have a great value for the industry.

As the fourth embodiment of this invention, a plasticizer may also be supplied to an ion-selective membrane for its regeneration by using an ion-concentration analyzer equipped with a regeneration system for the ion-selective membrane, which regeneration system is adapted to supply-discharge a plasticizer either identical in every aspects or analogous in effects to the plasticizer contained in the membrane to/from an ion-concentration measuring cell provided with an electrode which is in turn equipped with the ion-selective membrane containing an ion-selective material and the plasticizer.

In one aspect of this invention, there is thus provided an ion-concentration analyzer including an electrode unit of an ion-selective electrode equipped with an ion-selective membrane containing an ion-selective material and plasticizer and a reference electrode, an ion-concentration measurement system for determining the concentration of a specific ion species on the basis of an output from the electrode unit, an ion-concentration measurement cell provided with the electrode unit, and a test solution supply/discharge system for supplying-/discharging a test solution to/from the ion-concentration measurement cell. The analyzer further comprises a regeneration system of the ion-selective membrane for supplying to/discharging from the ion-concentration measurement cell a plasticizer which is identical in every aspects or analogous in effects to the plasticizer contained in the ion-selective membrane; and a control system adapted to actuate the test solution supply/discharge system in such a way that the test solution is supplied into the ion-concentration measurement cell upon measuring the concentration of the specific ion species in the test solution and discharged after the determination of the ion-concentration as well as adapted to actuate the regeneration system in such a way that the plasticizer is supplied into the ion-concentration measurement cell for at least part of the time period during which the concentration of the specific ion species is not measured.

Namely, as already mentioned in the above, in an ion-selective electrode of the neutral carrier type, a degraded ion-selective membrane may be regenerated efficiently with excellent reproducibility by supplying to the degraded ion-selective membrane a plasticizer either identical in every aspect or analogous in effects to the plasticizer initially contained in the membrane. On the basis of such finding, the fourth embodiment of this invention makes use of an ion-concentration analyzer per se for the regeneration of degraded ion-selective membranes by incorporating therein a simplified regeneration plasticizer supply system and making effective use of the time period during which the analyzer is not used for measurement.

As the regenerating plasticizer for the ion-selective membrane, it is possible to use any plasticizer so long as it has good miscibility to the base material of the membrane and has ability of dissolving the neutral carrier. For example, when a membrane is formed of polyvinyl chloride compounded with valinomycin and, as a plasticizer, dioctyl phthalate has been degraded, it may be regenerated by not only dioctyl phthalate but also dioctyl adipate which is different from dioctyl phthalate but which is analogous in effects to dioctyl phthalate.

Namely, by the expression "a plasticizer analogous in effects to the plasticizer initially contained in the ion-selective membrane," the former plasticizer being employed in the regeneration system, as used herein is meant such a plasticizer as mentioned above.

The fourth embodiment of this invention will hereinafter be described in more detail with reference to FIG. 14 which illustrates an ion-concentration analyzer embodying the features of the fourth embodiment. Namely, FIG. 14 is a simplified functional block diagram of an ion-concentration analyzer adapted to determine quantitatively $Na^+$ ions and $K^+$ ions contained in serum. In the drawing, numeral 1 indiates an $Na^+$ ion-selective electrode equipped with an $Na^+$ ion-selective membrane which contains monensin, a neutral carrier for a polyvinyl chloride membrane, and dioctyl adipate as a plasticizer. Designated at numeral 2 is a $K^+$ ion selective-electrode equipped with a $K^+$ ion-selective membrane formed of a polyvinyl chloride membrane which contains valinomycin as an ion-selective material and dioctyl adipate as a plasticizer. Numeral 3 indicates a silver/silver chloride electrode as a reference electrode. These electrodes 1, 2, 3 are housed as a unit in an ion-concentration determination cell (flow-cell) 4 to determine the concentrations of $Na^+$ ions and $K^+$ ions in each test solution. Numeral 5 represents a flow path of a test solution passing through the flow-cell 4. Shown at numeral 6 is a tube for introducing a sample of serum as a test solution for analysis. A dilution compartment is shown at numeral 7 and adapted to dilute the serum. Through a tube 8, a diluting and washing solution is introduced into the dilution compartment 7. The thus-introduced serum and solution diluent are mixed by a stirrer 9, which is driven by motor 10. Upon completion of an analysis of the thus-diluted serum, it is discharged as a waste liquid through a pipe 11. The test solution (i.e., diluted serum) is fed from the dilution compartment 7, through the flow-cell 4, into the pipe 11 by means of a pump 12. Designated at numeral 13 is a reservoir for storing the diluting and washing solution (which is used as both solution diluent and washing solution in the illustrated analyzer). The diluting and washing solution is fed to the dilution compartment 7 from the reservoir 13 by a pump 14. Numeral 15 indicates a solenoid valve which serves to cut off the flow of the test solution and/or diluting and washing solution between the dilution compartment 7 and flow-cell 4. Thus, a supply/discharge system of test solution is constructed by the reservoir 13 for the diluting and washing solution, dilution compartment 7, solenoid valve 15 and discharge pipe 11 for the test solution as well as pipes or tubes, pumps, etc. provided between the above elements. Numeral 16 indicates a measurement system for determining each potential of the ion-selective electrodes. A calculation and display system 17 is also incorporated to calculate and display, on the basis of measurement results of potentials appearing at the electrodes, the Na+ ion concentration and K+ ion concentration of serum.

A regenerating plasticizer is stored in a regenerating plasticizer reservoir 20, is allowed to controllably flow through valves 22, 23, and is drained through a drain pipe 24 into a regenerating plasticizer receptacle 21. A solenoid valve 25 ensures that no regenerating plasticizer be allowed to flow toward the pipe 11. A regeneration system is thus constructed by the regenerating plasticizer reservoir 20, regenerating plasticizer receptacle 21, valves 22, 23, etc. Incidentally, the flow path 5 is inclined toward the downstream to facilitate the flow of each test solution regenerating plasticizer or washing solution toward the pipes 11, 24. Numeral 18 indicates a control system adapted to control the operation of each of the solenoid valves 15, 25, valves 22, 23, motor 10, pumps 12, 14 and measurement system 16 as well as, if necessary, the calculation and display system 17. The control system 18 thus operates the supply/discharge system of test solution in such a way that a test solution is supplied into the ion-concentration measurement cell upon determining the concentrations of Na+ ions and K+ ions in the test solution and the test solution is discharged after the completion of the measurement of the Na+ and K+ ion concentrations. The control system 18 also actuates the measurement system when the test solution has been fed to the ion-concentration measurement cell. The control system 18 also serves to operate the regeneration system in such a way that it supplies the regenerating plasticizer into the ion-concentration measurement cell for at least part of the time period during which the analyzer is not applied for ion-concentration measurement and discharges the regenerating plasticizer from the ion-concentration measurement cell upon completion of the regeneration of the membranes. While no test solution is introduced through the tube 6, a washing system is established by the flow path 5, tube 8, dilution compartment 7, stirrer 9, motor 10, pumps 12, 14 and reservoir 13, whereby allowing it possible to wash the ion-selective electrodes and ion-concentration measurement cell.

The operation of the above analyzer is now described with respect to the analyses of the concentrations of Na+ ions and K+ ions in serum.

First of all, the valves 22, 23 are kept closed and the solenoid valve 25 is maintained in an open position.

While closing the solenoid valve 15, a predetermined amount of test serum is introduced through the tube 6 into the dilution compartment 7. Then, the diluting and washing solution is introduced in an amount 9 times that of the serum into the dilution compartment 7 by means of the pump 14. Here, the stirrer 9 is driven by the motor 10 to dilute the test serum by 10 times. The thus-obtained 10 times serum dilution is subsequently guided little by little towards the flow-cell 4 by opening the solenoid valve 15 and actuating the pump 12. When the flow path 5 for the test solution is filled with the 10 times serum dilution, potentials developed at the ion-selective electrodes 1, 2 are determined by the ion-selective electrodes 1, 2, reference electrode 3 and potential measurement systems 16. The measurement results of the potentials are thereafter delivered to the calculation and display system 17, where the Na+ ion and K+ ion concentrations in the test solution are analyzed and then displayed. During the above operation, the pump 12 is working. However, the pump 12 stops its operation as soon as the test solution is flowed in its entirety out of the dilution compartment 7. At the same time, the solenoid valve 15 is closed. Then, the dilution compartment 7 is filled with the diluting and washing solution. Thereafter, the solenoid valve 15 is opened again and the pump 12 is operated. This permits the washing and cleaning of the flow-cell 4, ion-selective electrodes 1, 2, and reference electrode 3. The pump 12 is operated until the flow path 5 and pipe 11 becomes free of the washing solution. Then, the solenoid valve 15 is closed and the ion-concentration measurement operation is reiterated. By the way, the calibration of the ion-selective electrodes 1, 2 may be carried out at any desired time by using a solution of known Na+ and K+ ion concentrations in lieu of serum beforehand in the ion-concentration analyzer illustrated in FIG. 14. Thereafter, the regeneration system constructed of the regenerating plasticizer reservoir 20, regenerating plasticizer receptacle 21, valves 22, 23, drain pipe 24, solenoid valve 25 and flow path 5 is operated for at least certain time period while the analyzer is not used for measurement. In order to regenerate the ion-selective membranes by immersing them in the regenerating plasticizer which is either identcal in every aspects or analogous in effects to the plasticizer initially contained in the membranes, it is necessary to open the valve 22 while maintaining the solenoid valves 15, 25 in closed positions. By controlling the opening degree of the valve 23, a predetermined amount of the regenerating plasticizer is caused to enter the regenerating plasticizer reservoir 20. This permits the regenerating plasticizer to flow naturally under the influence of gravity through the flow path 5 in the flow-cell 4 and then to drop, also naturally, from the drain pipe 24 into the regenerating plasticizer receptacle 21.

By controlling the opening degree of the valve 23 to adjust the amount of the regenerating plasticizer to be guided to the regenerating plasticizer reservoir 20 suitably, the ion-selective electrodes of the neutral carrier type can be dipped in the regenerating plasticizer for a predetermined time period while the analyzer is not used for analysis. Thus, it is possible to avoid the degradation of the ion-selective electrodes.

Na+ Ion-selective electrodes and K+ ion-selective electrodes of the neutral carrier type had life time as little as 1 month or so when used in conventional serum analyzers. Whenever they failed, it was necessary to replace them by fresh ones. Such ion-selective electrodes were however successfully employed for 6 months or more in the analyzer according to the fourth embodiment of this invention, by bringing from time to time them into contact with a regenerating plasticizer.

Owing to the provision of the analyzer according to the fourth embodiment of this invention, it has become feasible to use ion-selective electrodes of the neutral carrier type for a long time period even in the analysis of serum or for similar purposes. Thus, the present invention brings about, in accordance with its fourth embodiment, such merits that many electrodes can be saved per unit time period of measurement and, moreover, the overall period of suspension of the analyzer for the replacement of electrodes can be shortened. In addition, the analyzer according to the fourth embodiment of this invention is free from the danger that ion-selective membranes of the neutral carrier type may be swollen due to their over-dipping in a regenerating plasticizer since the present analyzer permits to immerse them only for a predetermined time period.

As the fifth embodiment of the present invention, the regeneration method of an ion-selective membrane may be carried out, without need for providing such a special regeneration system as in the analyzer used in the fourth embodiment of this invention, by using an ion-concentration analyzer equipped with a system capable of dissolving beforehand a plasticizer identical in every aspects or analogous in effects to the plasticizer initially incorporated in the ion-selective membrane in a washing solution which is used in a washing system for electrodes and ion-concentration measurement cell, or in a solution diluent which is used in an introduction/discharge system for test solution.

In one aspect of this invention, there is thus provided an ion-concentration analyzer equipped at least with an electrode unit including an ion-selective electrode having an ion-selective membrane made of a polymer membrane material and an ion selective material and plasticizer fixed thereon and a reference electrode, an ion-concentration measurement cell adapted to receive therein the electrode unit and a test solution, a system for introducing the test solution into the ion-concentration measurement cell and, after the measurement, discharging the test solution from the ion-concentration measurment cell, a system adapted to wash the electrode unit and ion-concentration measurement cell, an electric potential determination system for measuring a potential developed by the electorde unit, and a calculation and display system coupled with the electric potential determination system and adapted to calculate and display the concentration of a specific ion species in the test solution in accordance with a signal delivered from the electric potential determination system. The analyzer further comprises a system for dissolving a plasticizer identical in every aspects or analogous in effects to the first-mentioned plasticizer in the ion-selective membrane in a washing solution to be employed in the washing system or in a diluting solution to be used in the introduction/discharge system of the test solution.

The fifth embodiment of this invention will hereinafter be described in more detail with reference to FIG. 15, taking quantitative analyses of $Na^+$ and $K^+$ ions in serum as an example. In FIG. 15, numeral 1 indicates a sodium ion-selective electrode having a sodium ion-selective membrane made of polyvinyl chloride compounded with monensin (an ion-selective carrier) and dioctyl adipate (a plasticizer). Designated at numeral 2 is a potassium ion-selective electrode equipped with a potassium ion-selective membrane made of polyvinyl chloride compounded with valinomycin (an ion-selective material) and dioctyl adipate (a plasticizer). Numeral 3 represents a silver/silver chloride electrode which serves as a reference electrode. Numeral 4 indicates an ion-concentration measurement cell for the determination of $Na^+$ and $K^+$ ion concentrations in serum. Within the cell 4, there are housed a flow path 5 for each test solution and the electrodes 1, 2, 3. These electrodes are inserted with such positional relationship as shown in FIG. 15. The test solution is caused to flow from the left to the right in the drawing. At numeral 6, there is shown a tube for pouring each sample serum into a dilution compartment 7 which is also provided with another tube 8 for introducing a solution diluent and washing solution thereinto. In the dilution compartment 7, a predetermined amount of sample serum and a preset volume of the solution diluent are charged respectively through tubes 6, 8 and then agitated by a stirrer 10 which is driven by a motor 9, thereby formulating a test solution of a desired concentration.

The tube 8 communicates through a pump (feed pump) 11 with a reservoir 13 which stores therein a diluting and washing solution (for example, tris-buffer). The diluting and washing solution is thus fed by the pump 11 through the tube 8 to the dilution compartment 7.

The reservoir 13 is also communicated through a pump (feed pump) 16 with another reservoir 15 which stores therein a plasticizer 14 either identical in every aspects or analogous in effects to the plasticizer making up the ion-selective membranes of the electrodes 1, 2 (for example, dioctyl adipate). The plasticizer 14 is added to the diluting and washing solution 12 stored in the reservoir 13 by operating the pump 16.

A stirrer 17 is driven by a motor 18 and agitates an added portion of the plasticizer 14 with the diluting and washing solution 12 so as to facilitate the smooth dissolution of the added portion of the plasticizer 14 in the diluting and washing solution 12.

Designated at numeral 19 is a pipe (drain pipe) positioned downstream the flow path 5 and adapted to drain each test solution from the cell 4 after completion of its analysis. The drain pipe 19 is provided with a pump (drain pump) 20. The introduction or cut-off of the test solution into the cell 4 from the dilution compartment 7 is carried out by opening or closing a solenoid valve 21.

Accordingly, an introduction/discharge system is constructed by all the flow path 5, dilution compartment 7, tubes 6, 8 pipe 19, motors 9, 18, stirrers 10, 17, pumps 11, 16, 20, reservoirs 13, 15 and solenoid valve 21, whereby introducing a test solution into the cell 4 and discharging it from the cell 4 upon completion of its analysis. On the other hand, a washing and cleaning system is also established by all the flow path 5, dilution compartment 7, tube 8, motors 9, 18, stirrers 10, 17, pumps 11, 16 and reservoir 13, whereby washing and cleaning the electrodes 1, 2, 3 and cell 4.

Numeral 22 indicates a potential measurement system connected with the electrodes 1, 2, 3 and adapted to measure signals of potentials generated from the electrodes 1, 2, 3. The potential measurement system 22 is coupled with a calculation and display system 23, where the potential values are calculated on the basis of the signals of potentials, converted into $Na^+$ and $K^+$ ion concentrations and then displayed.

The solenoid valve 21, motor 9, pump 11, pump 16, pump 20, motor 18, potential measurement system 22 and calculation and display system 23 are actuated or deactuated respectively by operation commands (for example, electric signals) $P_1$, $P_2$, $P_3$, $P_4$, $P_5$, $P_6$, $P_7$, and $P_8$ from a control system 24. These operational commands are indicated by arrows in the drawing. Therefore, they perform such operations as formulation of each test solution introduction/discharge of each test solution into/from the cell, addition/agitation of the plasticizer to/with the diluting and washing solution, washing and cleaning of the dilution compartment, cell and electrode unit, determination of potential developed at each electrode, and calculation and display of each measured value.

The operation of the above analyzer is not described with respect to the analyses of the concentrations of $Na^+$ ions and $K^+$ ions in serum.

First of all, the motor 18 is rotated by the command $P_6$ to agitate the diluting and washing solution 12 by the stirrer 17. Then, the pump 16 is activated in accordance with the command $P_4$, thereby pouring a portion of the plasticizer 14 from the reservoir 15 into the reservoir 13. With the assistance of the stirrer 17, the thus-poured portion of the plasticizer 14 is caused to dissolve in the diluting and washing solution 12. It is preferred to saturate the diluting and washing solution 12 with the plasticizer 14.

Then, the command $P_1$ is generated to close the solenoid valve 21 and a predetermined amount of sample serum is charged through the tube 6 into the dilution compartment 7. The pump 11 is then activated by the command $P_3$ to charge a portion of the diluting and washing solution 12, which has been formulated as mentioned above and contains a portion of the plasticizer 14, into the dilution compartment 7 through the tube 8. The amount of the diluting and washing solution 12 is adjusted suitably so as to dilute the sample serum by 10 times. Thereafter, the motor 9 is turned on by the command $P_2$, to agitate the sample serum and diluting and washing solution by the stirrer 10, resulting in a formulation of a test solution of a predetermined concentration.

The solenoid valve 21 is then opened by the command $P_1$ and the pump 20 is activated in accordance with the command $P_5$, thereby introducing the test solution into the flow path 5 and causing it to flow through the cell 4. When the flow path 5 is filled up with the test solution, the commands $P_7$, $P_8$ are issued to activate the potential measurement system 22 and the calculation and display system 23, thereby measuring the potentials at the electrodes 1, 2, 3 and displaying the thus-measured values in terms of $Na^+$ and $K^+$ ion concentrations.

During the above operation, the pump 20 is kept running. However, it stops as soon as all the test solution has flowed out of the dilution compartment 7. Concurrently with the stopping of the pump 20, the solenoid valve 21 is also closed.

Then, the diluting and washing solution 12 with the plasticizer 14 dissolved therein is poured through the tube 8 into the dilution compartment 7 until the compartment 7 is filled up. By opening the solenoid valve 21 and activating the pump 20 again, the diluting and washing solution 12 with the plasticizer 14 is caused to pass through the flow path 5 and the electrodes 1, 2, 3, flow path 5 and cell 4 are thus washed and cleaned. Since the washing solution contains the regenerating plasticizer (for example, dioctyl adipate) which is either identical in every aspects or analogous in effects to the plasticizer making up the ion-selective membranes of the electrodes 1, 2, these ion-selective membranes are regenerated owing to the regenerating plasticizer while carrying out the washing and cleaning work. In other words, the membranes are degraded in activity upon conducting analysis but regenerated while washed and cleaned after the analysis.

After draining the above-mentioned washing solution completely from the dilution compartment 7, flow path 5 and pipe 19, the solenoid valve 21 is closed again to repeat the measurement of ion concentrations following the above-described operation.

The electrodes 1, 2 may be calibrated at any desired time points by providing the above analyzer with a supply system of a reference solution which contains $Na^+$ ions and $K^+$ ions in known concentrations.

Serum analyses were carried out using the analyzer according to the fifth embodiment of this invention and applying thereto electrodes which showed life time as little as one month in a conventional serum analyzer. The above electrodes were successfully used for at least 6 months without need for any replacement during that time period.

By using the analyzer according to the fifth embodiment of this invention, it has become feasible to employ ion-selective electrodes of the neutral carrier type even in serum analyses or for similar purposes over a long time period. Furthermore, the present analyzer has brought about such merits that many electrodes may be saved per unit time period, the analysis can be continued without interruption owing to the obviation of replacement of degraded electrodes, and the cumbersome calibration of electrodes has been made unnecessary although the calibration is indispensable whenever a fresh electrode is put on.

We claim:

1. A method for regenerating an ion-selective electrode equipped with an ion-selective membrane which is formed of a high polymer membrane containing an ion-selective material and plasticizer, which method comprises supplying to the ion-selective membrane a regenerating plasticizer which is either identical in every aspects or analogous in effects to the first-mentioned plasticizer and is capable of dissolving the ion-selective material therein and imparting flexibility to the ion-selective membrane.

2. The method according to claim 1, wherein the ion-selective membrane is a potassium ion-selective membrane formed of a polyvinyl chloride membrane which contains valinomycin as the ion-selective material and dioctyl adipate as the plasticizer.

3. The method according to claim 1, wherein the regenerating plasticizer is supplied to the ion-selective membrane by immersing a part of the ion-selective electrode, said part containing the ion-selective membrane, in the regenerating plasticizer for a certain period of time without removing the ion-selective membrane from the ion-selective electrode.

4. The method according to claim 1, wherein the regenerating plasticizer is supplied to the ion-selective membrane by dispersing in the ion-selective membrane a carrier containing the regenerating plasticizer in a concentration higher than the concentration of the plasticizer still remaining in the ion-selective membrane.

5. The method according to claim 1, wherein the regenerating plasticizer is supplied to the ion-selective membrane by providing in the ion-selective electrode a built-in plasticizer-supplying pocket, which is filled with the regenerating plasticizer, in such a way that a part of the boundary wall of the pocket is formed of a part of the ion-selective membrane.

6. The method according to claim 1, wherein the regenerating plasticizer is supplied to the ion-selective membrane by incorporating, in an ion-concentration analyzer, means for supplying-discharging the regenerating plasticizer to/from its ion-concentration measuring cell in which the ion-selective electrode is provided.

7. The method according to claim 1, wherein the regenerating plasticizer is supplied to the ion-selective membrane by incorporating, in an ion-concentration analyzer, means for dissolving in advance the regenerating plasticizer in a washing solution to be employed in a washing system of the ion-selective electrode and its ion-concentration measuring cell or a diluting solution to be employed in an introduction/discharge system of each test solution into/from the cell.

8. The method according to claim 7, wherein the regenerating plasticizer is dissolved in the diluting solution.

9. An ion-selective electrode for practicing the method of claim 4, equipped with a casing filled with an electrically conductive material, an ion-selective membrane attached to a free end portion of the casing, an inner reference electrode supported within the casing and a lead connected to the internal reference electrode, wherein the ion-selective membrane contains a polymer as its base material, the polymer contains in turn an ion-selective material and plasticizer as well as a carrier containing therein another plasticizer, and the latter plasticizer is present in a concentration higher than the former plasticizer.

10. The electrode according to claim 9, wherein the carrier is selected from the group consisting of diatomaceous earth, activated carbon, silica gel, alumina, activated clay and molecular sieve.

11. The electrode according to claim 9, wherein 1~5 wt.% of the carrier is contained in the ion-selective membrane.

12. An ion-selective electrode for practicing the method of claim 5, including a hollow cylindrical electrode casing defining an opening at one end thereof, an ion-selective membrane hermetically attached over the opening and made of a high polymer membrane containing an ion-selective material and plasticizer, a partition wall dividing the interior of the cylindrical electrode case into a first cell including the opening and a second cell positioned opposite to the opening, an ion-conductive material sealed in the first cell, an inner reference electrode immersed in the ion-conductive material and kept in place by the partition wall and a lead extending from the inner reference electrode to the outside of the cylindrical electrode casing through the second cell, wherein said electrode further comprises:

a third cell which is a pocket formed in a base portion of the first chamber and includes a part of the ion-selective membrane as a part of its boundary wall, said third cell being filled with a plasticizer which is either identical in every aspects or analogous in effects to the plasticizer contained in the ion-selective membrane and is capable of dissolving the ion-selective material therein and imparting flexibility to the ion-selective membrane;

an air flow passage extending from the third cell to the second cell; and another membrane hermetically attached over the opening of the air flow passage into the second cell, said membrane being permeable to air but impervious to the plasticizer in the third cell.

13. An ion-concentration analyzer for practicing the method of claim 6, including an electrode unit of an ion-selective electrode equipped with an ion-selective membrane containing an ion-selective material and plasticizer and a reference electrode, an ion-concentration measurement system for determining the concentration of a specific ion species on the basis of an output from the electrode unit, an ion-concentration measurement cell provided with the electrode unit, and a test solution supply/discharge system for supplying/discharging a test solution to/from the ion-concentration measurement cell wherein said analyzer further comprises:

a regeneration system of the ion-selective membrane for supplying to/discharging from the ion-concentration measurement cell a plasticizer which is identical in every aspects or analogous in effects to the plasticizer contained in the ion-selective membrane; and a control system adapted to actuate the test solution supply/discharge system in such a way that the test solution is supplied into the ion-concentration measurement cell upon measuring the concentration of the specific ion species in the test solution and discharged after the determination of the ion-concentration as well as adapted to actuate the regeneration system in such a way that the plasticizer is supplied into the ion-concentration measurement cell for at least part of the time period during which the concentration of the specific ion species is not measured.

14. An ion-concentration analyzer for practicing the method of claim 7, equipped at least with an electrode unit including an ion-selective electrode having an ion-selective membrane made of a polymer membrane material and an ion-selective material and plasticizer fixed thereon and a reference electrode, an ion-concentration measurement cell adapted to receive therein the electrode unit and a test solution, a system for introducing the test solution into the ion-concentration measurement cell and, after the measurement, discharging the test solution from the ion-concentration measurement cell, a system adapted to wash the electrode unit and ion-concentration measurement cell, an electric potential determination system for measuring a potential developed by the electrode unit, and a calculation and display system coupled with the electric potential determination system and adapted to calculate and display the concentration of a specific ion species in the test solution in accordance with a signal delivered from the electric potential determination system, wherein the analyzer further comprises a system containing a plasticizer for dissolving said plasticizer identical in every aspect or analogous in effects to the first-mentioned plasticizer in the ion-selective membrane in a washing solution to be employed in the washing system or in a diluting solution to be used in the introduction/discharge system of the test solution.

* * * * *